US011078545B2

(12) United States Patent
Birkner

(10) Patent No.: US 11,078,545 B2
(45) Date of Patent: Aug. 3, 2021

(54) DETECTION OF BACTERIAL (MOLLICUTES) CONTAMINATION

(71) Applicant: Roche Diagnostics Operations, Inc., Indianapolis, IN (US)

(72) Inventor: Christian Birkner, Uffing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 212 days.

(21) Appl. No.: 15/626,641

(22) Filed: Jun. 19, 2017

(65) Prior Publication Data
US 2017/0292148 A1 Oct. 12, 2017

Related U.S. Application Data

(63) Continuation of application No. 14/549,647, filed on Nov. 21, 2014, now abandoned, which is a continuation of application No. 13/364,050, filed on Feb. 1, 2012, now abandoned, which is a continuation of application No. PCT/EP2010/004655, filed on Jul. 29, 2010, now abandoned.

(30) Foreign Application Priority Data

Aug. 1, 2009 (EP) ..................... 09009965

(51) Int. Cl.
*C12Q 1/689* (2018.01)
*C12Q 1/6848* (2018.01)
*C12Q 1/686* (2018.01)

(52) U.S. Cl.
CPC ............ *C12Q 1/689* (2013.01); *C12Q 1/686* (2013.01); *C12Q 1/6848* (2013.01); *C12Q 2527/125* (2013.01); *C12Q 2527/137* (2013.01); *C12Q 2549/125* (2013.01)

(58) Field of Classification Search
CPC ...... C12Q 1/689; C12Q 1/686; C12Q 1/6848; C12Q 2527/137; C12Q 2527/125; C12Q 2549/125
See application file for complete search history.

(56) References Cited

U.S. PATENT DOCUMENTS

| 2008/0318801 A1 | 12/2008 | Leung |
| 2009/0217399 A1 | 8/2009 | Stern et al. |
| 2011/0091885 A1 | 4/2011 | Schmitt et al. |

FOREIGN PATENT DOCUMENTS

| CN | 100999763 A | 7/2007 |
| CN | 101492741 A | 7/2009 |

OTHER PUBLICATIONS

Gunson et al. Journal of Clinical Virology 2008; 43: 372-375 (Year: 2008).*
Haugland et al. Water Research 2005; 39: 559-568 (Year: 2005).*
Fredricks, D.N. and Relman, D.A. Journal of Clinical Microbiology 1998; 36: 2810-2816 (Year: 1998).*
Barile M.F., Hopps H.E., Grabowski M.W. (1978) Incidence and Sources of Mycoplasma Contamination: A Brief Review. In: McGarrity G.J., Murphy D.G., Nichols W.W. (eds) Mycoplasma Infection of Cell Cultures. Cellular Senescence and Somatic Cell Genetics, vol. 3. Springer, Boston, MA. (Year: 1978).*
Harasawa et al. Research in Microbiology 1993; 144: 489-493 (Year: 1993).*
Widjaja et al. Virology 2006; 350: 137-145 (Year: 2006).*
Kojima et al. Journal of Veterinary Medical Science 1996; 58: 1045-1048 (Year: 1996).*
Bastian, Frank O. et al., *Spiroplasma* spp. from transmissible spongiform encephalopathy brains or ticks induce spongiform encephalopathy in ruminants, Journal of Medical Microbiology, 2007, pp. 1235-1242, vol. 56.
Bastian, Frank O., Spiroplasma as a Candidate Agent for the Transmissible Spongiform Encephalopathies, Journal of Neuropathology and Experimental Neurology, 2005, pp. 833-838, vol. 64, No. 10.
Brown, D. B. et al., Assay Validation for Rapid Detection of Mycoplasma Contamination, BioProcess International, 2009, pp. 30-40.
Eldering, Joyce A. et al., Development of a PCR method for mycoplasma testing of Chinese hamster ovary cell cultures in the manufacture of recombinant therapeutic proteins, Biologicals, 2004, pp. 183-193, vol. 32.
International Search Report dated Dec. 2, 2010, in Application No. PCT/EP2010/004655, 3 pages.
Osborne, Catherine A. et al., PCR-generated artefact from 16S rRNA gene-specific primers, FEMS Microbiology Letters, 2005, pp. 183-187, vol. 248.
Roche Diagnostics GmbH, MycoTOOL PCR Mycoplasma Detection Kit, Cat No. 05 200 709 001, 2008, 2 pps.
Scahill, Shaun J. et al., Expression and characterization of the product of a human immune interferon cDNA gene in Chinese hamster ovary cells, Proceedings of the National Academy of Sciences USA, 1983, pp. 4654-4658, vol. 80.
Schmitt, Maruks and Pawlita, Michael, High-throughput detection and multiplex identification of cell contaminations, Nucleic Acids Research, 2009, 8 pages, vol. 37, No. 18, e119.
Stratagene, Gene Characterization Kits, 1988 Catalog, 2 pps.

(Continued)

*Primary Examiner* — Angela M. Bertagna
(74) *Attorney, Agent, or Firm* — Stinson LLP

(57) ABSTRACT

The present disclosure provides a method and system for the PCR amplification of a target sequence which suppresses non-specific amplification products. The disclosure concerns the use of a primer pair optimized to amplify a nucleic acid of a contaminant in the background of genomic DNA of a first organism. When DNA from a second organism suspected for comprising the contaminant is subjected to the same PCR-based amplification reaction, detection sensitivity and specificity of the contaminant is enhanced when an amount of genomic DNA of the first organism is present in the amplification reaction.

6 Claims, 14 Drawing Sheets

Specification includes a Sequence Listing.

(56) References Cited

OTHER PUBLICATIONS

Van Pelt-Verkuil, E. et al., Taq and Other Thermostable DNA Polymerases, Principles and Technical Aspects of PCR Amplification, 2008, pp. 103-118, Ch. 7.

Weiner, Michael P. and Slatko, Barton E., Kits and their unique role in molecular biology: a brief retrospective, BioTechniques, 2008, pp. 701-704, vol. 44.

Wong-Lee, Jolene G. and Lovett, Michael, Rapid and Sensitive PCR Method for Identification of Mycoplasma Species in Tissue Culture, Diagnostic Molecular Microbiology, 1993, pp. 257-260.

Zhi, Yan et al., Validation of a PCR method for the detection of mycoplasmas according to European Pharmacopoeia section 2.6.7, Biologicals, 2010, pp. 232-237, vol. 38.

\* cited by examiner

DETECTION OF BACTERIAL (MOLLICUTES) CONTAMINATION

RELATED APPLICATIONS

This application is a continuation of U.S. application Ser. No. 14/549,647 filed Nov. 21, 2014 (abandoned), which is a continuation of U.S. application Ser. No. 13/364,050 filed Feb. 1, 2012 (abandoned), which is a continuation of International Application No. PCT/EP2010/004655 filed Jul. 29, 2010, which claims the benefit of European Patent Application No. 09009965.6 filed Aug. 1, 2009, the disclosures of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jan. 31, 2012, is named Sequence_Listing_26237_US.txt, and is 1,128 bytes in size.

BACKGROUND

Field of the Disclosure

The present disclosure relates to contamination within biological samples. More specifically, the instant disclosure relates to a system and method for detecting bacterial contamination within biological samples.

Description of the Related Art

*Mycoplasma* is a genus of bacteria belonging to the class of Mollicutes which lack a cell wall. Without a cell wall, *mycoplasma* bacteria are unaffected by many common antibiotics such as penicillin or other beta-lactam antibiotics that target prokaryotic cell wall synthesis. There are over 100 recognized species of the genus *Mycoplasma*, one of several genera in the Mollicutes. Mollicutes are parasites or commensals of humans, other animals (including insects), and plants (although the genus *Mycoplasma* is by definition restricted to vertebrate hosts).

Cholesterol is required for the growth of species of the genus *Mycoplasma*, as well as certain other genera of mollicutes. The optimum growth temperature of such species is often the temperature of their host, if the host is warm-bodied (e.g., 37° C. in humans), or ambient temperature if the host is unable to regulate its own internal temperature. Analysis of 16S ribosomal RNA sequences, as well as gene content, strongly suggest that mollicutes, including the genus mycoplasmas, are closely related to either the *Lactobacillus* or the *Clostridium* branch of the phylogenetic tree (*Firmicutes sensu stricto*).

*Mycoplasma* species are often found in research laboratories as contaminants in cell culture. *Mycoplasma* cell culture contamination can occur due to contamination from individuals or contaminated cell culture medium ingredients, for example. *Mycoplasma* cells are physically small—less than 1 μm—and are difficult to detect with a conventional microscope. Mycoplasmas may induce cellular changes, including chromosome aberrations, changes in metabolism and cell growth. Severe *Mycoplasma* infections have the potential to destroy a cell line.

Mycoplasmas are also involved as pathogens in a number of diseases. For example, *mycoplasma pneumoniae* is the major causative agent of community-acquired pneumonia.

*Spiroplasma* is another genus of bacteria belonging to the class of Mollicutes. Species of the genus *Spiroplasma* have been linked with the transmissible spongiform encephalopathies (TSEs) scrapie in sheep, chronic wasting disease (CWD) in deer, and Creutzfeldt-Jakob disease in humans (*Spiroplasma* species isolates from both scrapie-affected sheep brain and CWD-affected deer brain which was inoculated intra-cranially into sheep and goat, respectively, induced spongiform encephalopathy resembling natural TSE in these animals). However, such linkage is considered controversial (see, Alexeeva, I., et al., J Clin Microbiol 44 (2006) 91-97, were a blinded study of rRNA species failed to detect any footprint of *Spiroplasma* in scrapie-infected hamster brain).

*Spiroplasma* bacteria have also been shown to grow in embryonated eggs and can be passaged in such a culture system. Embryonated eggs play a major role in the production of vaccines. For example, human vaccines against influenza have been available for almost 60 years and, until recently, were prepared almost entirely from viruses grown in the allantoic cavity of 9 to 11 day old embryonated chicken eggs.

Moreover, the possibility of *Mycoplasma* contamination during biopharmaceutical production, cell therapy, and tissue engineering is also a concern and potential major problem. Traditional detection methods, which are required by drug regulators worldwide, use growth on culture media to identify contaminating organisms. These culture-based techniques require a long time to achieve results. Furthermore, cultivation of certain *Mycoplasma* species may not be possible or reliable. Therefore, an improved, more rapid, and more reliable microbial assay is needed.

SUMMARY OF THE DISCLOSURE

The present disclosure provides an improved PCR-based amplification of a target sequence by suppressing non-specific amplification products. This improvement concerns the use of a primer pair optimized to amplify a nucleic acid of a contaminant in the background of genomic DNA of a first organism. When DNA from a second organism, suspected as comprising the contaminant, is subjected to the same polymerase chain reaction (PCR) based amplification reaction, detection sensitivity and specificity of the contaminant is enhanced when an amount of genomic DNA of the first organism is present in the amplification reaction.

According to an embodiment of the instant disclosure, an improved method for determining the presence or absence of a bacterial contaminant in a liquid sample with biological material is provided. The method includes the steps of processing the sample and purifying the nucleic acids from the processed sample, forming a composition (reaction mixture) for a PCR-based amplification reaction, performing PCR, and detecting the presences or absence of an amplified target sequence. According to such embodiments, the composition includes a first primer according to SEQ ID NO: 1, a second primer according to SEQ ID NO:2, and the purified nucleic acid of the processing (and purifying) step or a measured fraction thereof as a template. Also, according to such embodiments, the presence of an amplified target sequence indicates the presence of the bacterial contaminant in the sample, and the absence of said amplified target sequence indicates the absence of the bacterial contaminant in the sample.

According to some embodiments, relative to the volume of the sample, a predetermined amount of DNA from CHO cells is added to at least one of the sample, the processed sample, the purified nucleic acids, or the reaction mixture. In such embodiments, the added DNA from CHO cells reduces unspecific amplification in the step of detecting.

Another embodiment of the instant disclosure provides a composition comprising amniotic fluid from embryonated eggs and DNA from CHO cells.

According to another embodiment of the instant disclosure, a composition is provided which comprises purified nucleic acids from a sample and DNA from CHO cells (which is free of prokaryotic DNA). According to such embodiments, the sample (from which the purified DNA is obtained) is selected from the group consisting of amniotic fluid, a suspension of eukaryotic cells, and a supernatant from a suspension of eukaryotic cells.

According to yet another embodiment of the instant disclosure, a process for amplifying DNA of a prokaryotic contaminant in DNA isolated from a sample selected from the group consisting of amniotic fluid, a suspension of eukaryotic cells, and a supernatant from a suspension of eukaryotic cells is provided. Such processes, according to the instant disclosure, include the use of a reaction mixture and/or composition as disclosed herein.

Yet other embodiments of the present disclosure include kits comprising a lysis reagent, purified DNA from CHO cells at a predefined concentration, a first primer according to SEQ ID NO:1 and a second primer according to SEQ ID NO:2. The DNA from the CHO cells is free of prokaryotic DNA. According to some embodiments of these kits, some or all of the components are provided in separate containers.

According to yet other embodiments of the instant disclosure, an improved method for performing a PCR is provided. In such embodiments, a specific amplification product having a size in the range of about 100 base pairs (bp) to about 1500 bp is formed by DNA polymerase-catalyzed extension of a pair of oligonucleotide primers. The improved method includes the steps of providing a pair of oligonucleotide primers; providing genomic DNA of a first eukaryotic organism; providing a third template comprising genomic DNA of a second eukaryotic organism which is suspected to contain genomic DNA of said one or more prokaryotic organism; mixing the pair of primers into a reaction mixture and also mixing into the relation mixture the third template and a measured amount of the genomic DNA of the first eukaryotic organism, and performing PCR under conditions such that the formation of non-specific PCR amplification product is suppressed.

According to embodiments of such improved method for performing PCR, each of the primers hybridize to the target sequence comprised in the genomic complement of the 16S-rRNA of one or more prokaryotic organism(s). The pair of oligonucleotide primers is capable of forming a specific amplification product from a first template and the PCR is conducted under predetermined conditions in a reaction mixture having a predetermined composition. The first template comprises genomic DNA of a first eukaryotic organism and genomic DNA of the one or more prokaryotic organism(s). Also, the pair of oligonucleotide primers (during PCR) does not form an amplification product from a second template under the same conditions in the reaction mixture. Furthermore, according to such embodiments, the second template genomic DNA of the one or more prokaryotic organism(s) is absent but genomic DNA of the first eukaryotic organism is comprised.

BRIEF DESCRIPTION OF THE DRAWINGS

The features of this disclosure, and the manner of attaining them, will become more apparent and the disclosure itself will be better understood by reference to the following description of embodiments of the disclosure taken in conjunction with the accompanying drawing.

Figure 1:
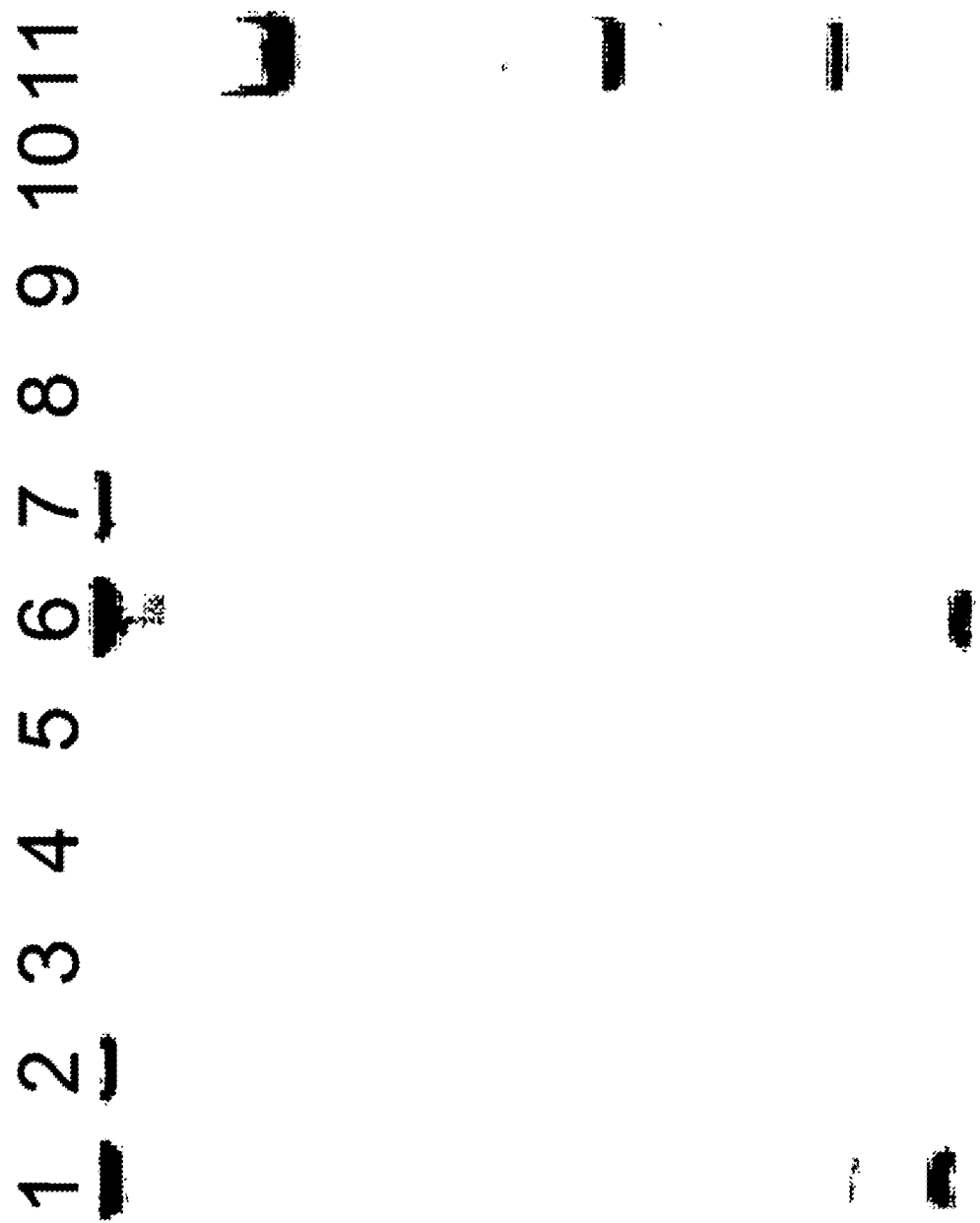
FIG. 1 is a gel showing PCR amplification products (of GAPDH-specific primers) obtained from a MDCK cell culture without the addition of CHO DNA.

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

BRIEF DESCRIPTION OF THE SEQUENCE LISTING

SEQ ID NO.: 1 is a universal primer (forward) for the detection of *Mycoplasma* and related species.

SEQ ID NO.: 2 is a universal primer (reverse) for the detection of *Mycoplasma* and related species.

SEQ ID NO.: 3 is a forward primer specific for a target sequence in the Glyceraldehyde 3-phosphate dehydrogenase gene (control sequence).

SEQ ID NO.: 4 is a reverse primer specific for a target sequence in the Glyceraldehyde 3-phosphate dehydrogenase gene (control sequence).

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

Certain terms are used with particular meaning, or are defined for the first time, in this description of the present disclosure. For the purposes of the present disclosure, the terms used are defined by their art-accepted definitions, when such exist, except that when those definitions conflict or partially conflict with the definitions set forth below. In the event of a conflict in definition, the meaning of a term is first defined by any of the definitions set forth below.

The term "comprising" is used in the description of the disclosure and in the claims to mean "including, but not necessarily limited to".

The articles "a" and "an" are used herein to refer to one or to more than one (i.e. to at least one) of the grammatical object of the article. By way of example, "a microorganism" means one microorganism or more than one microorganism.

When designating a range of numerical values such as a concentration range, the range may be indicated by the word "between", followed by a first value $n_1$, the word "and", and a second value $n_2$. In addition, the designated range can be indicated by the expression "in the range of $n_1$ to $n_2$". If not stated otherwise, when a designated range is indicated, the lower boundary of the designated range is understood as being the value either equal to, or higher than the first value. The higher boundary of the designated range is understood as being either the value equal to, or lower than the second value". Thus, a value x in the designated range is given by $n_1 \leq x \leq n_2$.

Further, it is understood that the term "about" in combination with a numerical value n indicates a value x in the interval given by the numerical value±5% of the value, i.e. $n-0.05*n \leq x \leq n+0.05*n$.

The term "sample" as used herein refers to a complex sample, such as a biological sample, i.e., a sample with biological material. The sample may contain a plurality of organic and inorganic compounds which are desired to be separated from nucleic acids comprised in the biological material. The term "sample" may also encompass an aqueous solution containing nucleic acids derived from other origins, e.g. from chemical or enzymatic reaction mixtures, or from a previous purification of biological sample material. The term biological sample, from which nucleic acids are purified, may encompass samples comprising viruses or bacterial cells, as well as isolated cells from multicellular organisms such as human and animal cells, as well as primary cultures of tissue and cultures of cell lines, as well as supernatants and rinses thereof. The present disclosure also encompasses biological samples such as a fluid from the human or animal body. For example, the sample can be whole blood, blood serum, blood plasma, cerebral fluid, sputum, stool, biopsy specimens, bone marrow, oral rinses, tissues, urine, or mixtures thereof.

According to one embodiment of the disclosure, the sample may be a "liquid sample", i.e. the sample is in a fluidic state and the sample fluid comprises water and a biological material. The biological material may comprise cells or cellular components. According to some embodiments, the liquid sample is selected from the group consisting of a cell culture supernatant, a suspension of cultured cells, and an amniotic fluid. In some embodiments, the amniotic fluid is from embryonated avian eggs.

For the purpose of the present disclosure, the meaning of the term "processing" or "processed," in combination with "liquid sample," is that the sample is treated by adding one or more compounds, and mixing the one or more compounds with the liquid sample, thereby resulting in a "processed sample". An exemplary compound which can be used for such treatment may be selected from the group consisting of a detergent, a surfactant, an organic solvent, a chaotropic agent, a protease, and a nuclease inhibiting agent. A "chaotropic agent," according to the present disclosure, includes any chemical substance which disturbs the ordered structure of liquid water. A chaotropic agent, as referred to herein, may also facilitates unfolding, extension, and dissociation of proteins.

An exemplary processed sample according to the instant disclosure includes a lysate. A "lysate" or a "lysed sample" may be obtained from a cell or plurality of cells, such as microbial cells and bacterial cells, wherein the structural integrity of a substantial portion of the cells present is disrupted. To this end, the cell wall, if present, may be destroyed for releasing the contents within the cell. To release the contents of disrupted cells, such as bacterial cells, the material is treated with certain agents to disintegrate, make porous, dissolve, degrade, and/or denature the cell walls of the microbial cells. In addition to the above, the cellular membranes may be destroyed. To release the contents of cells, tissue or, more generally, from the particles which are comprised in the biological sample, the material may be treated with enzymes or with chemicals to dissolve, degrade or denature the cellular walls and cellular membranes of the cells or such organisms. In any case the lysis ("lytic") process will also disrupt the structural integrity of any bacterial contaminant (within the sample), thereby liberating nucleic acids of a contaminant.

For the lytic process it is common to use chaotropic agents such as a guanidinium salt and/or anionic, cationic, zwitterionic, or non-ionic detergent when nucleic acids are set free in the process. It is also fairly common to use proteases which rapidly degrade enzymes with nucleolytic activity and other unwanted proteins. In case there remains particulate, i.e. undissolved matter of the sample material following the lysis process, the particulate matter can be separated from the lysate to result in a cleared lysate which may be done by filtering or centrifugation, for example. Thus, the term "lysate" encompasses a cleared lysate.

"Purification of nucleic acids" from a processed sample can be done using a wide variety of methods which are standard techniques. These may include, for example, precipitation of nucleic acids from an aqueous solution using an alcohol (e.g., ethanol or isopropanol, for example), and isolation of the precipitate. Other methods may include adsorption of nucleic acids onto a solid phase (for example, with an oxidic surface such as silica), separating the solid phase, and eluting the nucleic acids from the solid phase.

The "polymerase chain reaction" ("PCR") is a technique for amplifying a single or few copies of a particular target DNA sequence across several orders of magnitude, wherein copies of the DNA sequence are generated. PCR relies on thermal cycling, consisting of cycles of repeated heating and cooling of the reaction mixture, thereby effecting DNA melting and enzymatic replication of the DNA. Primers (DNA oligonucleotides) containing sequences complementary to the target DNA sequence along with a DNA polymerase are key components to enable selective and repeated amplification. As PCR progresses, the DNA generated (also known as an "amplicon") is itself used as a template for replication, setting in motion a chain reaction in which the DNA template is exponentially amplified. A "reaction mixture" in this regard comprises a DNA polymerase, dNTP, ions, buffer and all other compounds necessary to affect extension of the primers hybridized (annealed) to the target DNA sequence.

In some cases, PCR occasionally produces irregular amplicons or artifacts (i.e. non-specific amplification of fragments differing in size from the desired target DNA fragment). For example, PCR performed using a primer pair of SEQ ID NOs: 1 and 2 (according to the PCR reaction conditions set forth in Eldering, J. A., et al., Biologicals 32 (2004) 183-193, which discloses a system for bacterial testing of Chinese hamster ovary cells, the disclosure of which is hereby incorporated by reference in its entirety) occasionally produces non-specific amplification products. This is especially so when the DNA template is prepared from sample material from cultures of cells derived from other animal species or humans is used as template. However, as surprisingly and unexpected discovered and disclosed by the instant disclosure, the formation of non-specific amplification products and artifacts can be significantly suppressed when the PCR (utilizing pairs according to SEQ ID NOs: 1 and 2 and the reaction conditions set forth in Eldering, et al.) is performed in the presence of CHO cell DNA. As disclosed herein, this desired technical effect is most beneficial when the CHO cell DNA is free of contamination with bacterial DNA which can be amplified by the primer pair.

According to an embodiment of the present disclosure, a method for performing PCR is provided. The method includes processing and/or purifying nucleic acid from a sample (such as a eukaryotic sample suspected as having a bacterial contamination). Preparing a PCR reaction mixture including primers specific for a first target, such as a contaminant nucleic acid sequence (from a prokaryotic source, for example) within the sample, and adding in nucleic acid from a second source, for example a second eukaryotic sample. The method further includes performing PCR and detecting the specific amplification product. As disclosed herein, the instant method surprisingly and unexpectedly reduces and/or eliminates non-specific amplification products.

According to an embodiment of the instant disclosure, an improved method for performing PCR is provided. According to such embodiments, a specific amplification product with a size in the range of about 100 bp to about 1500 bp is formed by DNA polymerase-catalyzed extension of a pair of oligonucleotide primers during PCR. The primers each hybridize to a target sequence comprising the genomic complement of the 16S-rRNA of one or more prokaryotic organism(s) and the pair of oligonucleotide primers is capable of forming (in PCR) a specific amplification product from a first template (under predetermined reaction conditions and compositions). According to such embodiments, the first template comprises genomic DNA of a eukaryotic organism and genomic DNA of one or more prokaryotic organism. As noted above, according to such embodiments, the pair of primers hybridizes to target sequences within the genomic complement of rRNA of the one or more prokaryotic organisms and does not form an amplification product (under the same conditions) from genomic DNA of the eukaryotic organism of the first template. Furthermore, the pair of primers does not form an amplification product (under the same conditions) from genomic DNA from an additional eukaryotic organism (such as CHO cells).

According to some embodiments of the improved method for performing PCR, the improved method comprises the steps of: (a) providing a pair of oligonucleotide primers; (b) providing genomic DNA of a first eukaryotic organism; (c) providing a third template comprising genomic DNA of a second eukaryotic organism which is suspected to contain genomic DNA of one or more prokaryotic organism(s); (d) mixing in the reaction mixture the primer pair of (a), the third template of (c), and a measured amount of the genomic DNA of the first eukaryotic organism of (b), and performing PCR under the conditions; wherein the formation of a non-specific PCR amplification product is suppressed.

In the context of the present disclosure, the reaction conditions of the PCR reflect parameters including temperature regime, incubation times, number of PCR cycles and other physical parameters as known in the art of PCR. For example, the reaction mixture comprises all components of the final mixture with which the PCR process is conducted, including all compounds needed for primer elongation. The reaction mixture also includes the pair of primers, each at its respective predetermined concentration. It should be understood, that reaction parameters and mixtures may vary based on variables such as the PCR platform being used, the volume of the reaction mixture, etc. The present disclosure, and the methods disclosed herein, are not limited to any one amplification platform and are applicable with all platforms for amplifying and/or detecting the presence (and/or quantifying) DNA or RNA. Further, and for the sake of clarity, the reaction mixture in this sense does not comprise the template DNA which is added separately (following its processing and purification).

According to the instant disclosure, a template DNA may comprise genomic DNA of a first organism (such as a eukaryotic organism suspected of having bacterial contamination) and then additionally, DNA from another additional organism in a measured amount (e.g., based on the amount of DNA from the first organism). According to an exemplary embodiment of such embodiments, the additional organism may be CHO cells. According to such exemplary embodiment, CHO cell DNA is added to the PCR reaction mixture in a measured amount (i.e. at a predetermined concentration which may be based on the amount of target and/or volume of the reaction mixture, for example).

In another embodiment of the instant disclosure, the pair of oligonucleotide primers hybridizes to a plurality of prokaryotic species, and between 0 to 3 mismatches may occur in the hybridization of the primers with their target region of the 16S-rRNA gene of such prokaryotic species. According to some embodiments, a mismatch (if present) would not be at the terminal nucleotide providing the 3'-OH group of the respective oligonucleotide.

In another embodiment of the instant disclosure, the one or more prokaryotic organism(s) may be a species selected from the group consisting of a Mollicutes species, a *Bacillus* species, a *Clostridium* species, a *Corynebacterium* species, a *Micrococcus* species, a *Staphylococcus* species, and a *Streptococcus* species. Further, the species may be a *Mycoplasma* species such as *M. hyorhinis, M. arginini, M. pneumoniae, M. fermentans, M. orale*, and *M. pirium*. Additionally the species may be an *Acholeplasma* species, *Acholeplasma laidlawii*, or a *Spiroplasma* species such as *Spiroplasma mirium*.

In another embodiment of the disclosure, the additional eukaryotic organism is a CHO cell or a culture comprising a plurality of CHO cells. Also, in some embodiments the pair of primers comprises either one of, or both of, SEQ ID NO:1 and SEQ ID NO:2. In yet other embodiments of the disclosure the conditions and the reaction mixture comprise those as specified in the MYCOTOOL assay by Roche Diagnostics GmbH, Mannheim (Germany) described in the manuals of the MYCOTOOL test kits (catalog numbers, 05200709001; 05184592001; 05184240001, for example).

Another embodiment of the present disclosure provides an improved method for determining the presence or absence of a bacterial contaminant in a liquid sample, said method comprising the steps of: (a) processing the sample and purifying the nucleic acids from the processed sample; followed by (b) forming a composition for a PCR-based amplification reaction, the composition including a first primer according to SEQ ID NO:1, a second primer according to SEQ ID NO:2, and the purified nucleic acids of step (a) or a measured fraction thereof as a template; followed by (c) performing a polymerase chain reaction (PCR) with the composition of step (b), whereby a target sequence comprised in a prokaryotic 16S-rRNA gene, if present in the template, is amplified; followed by (d) detecting the presence or absence of an amplified target sequence, whereby the presence of said amplified target sequence indicates the presence of the bacterial contaminant in the sample, and the absence of said amplified target sequence indicates the absence of the bacterial contaminant in the sample; with the improvement being characterized in that relative to the volume of the sample a predetermined amount of DNA from CHO cells is added to (i) the sample, or (ii) the processed sample of step (a), or (iii) the purified nucleic acids obtained in step (a), or (iv) the composition of step (b) whereby the added DNA from CHO cells reduces unspecific amplification in step (d).

In some embodiments of such method, the predetermined amount of DNA per ml of the liquid sample is the DNA content from about $5 \times 10^6$ CHO cells. In some embodiments the liquid sample is selected from the group consisting of cell culture medium with cultured cells, cell-free culture supernatant, and amniotic fluid. In embodiments in which the liquid sample comprises amniotic fluid, the amniotic fluid is from embryonated eggs.

According to even further embodiments of the improved method for determining the presence or absence of a bacterial contaminant in a liquid sample, provided by the instant disclosure, the bacterial contaminant is a genus selected from the group consisting of *Acholeplasma, Bacillus, Clostridium, Corynebacterium, Micrococcus, Mycoplasma, Spiroplasma, Staphylococcus*, and *Streptococcus*. In some further embodiments, the bacterial contaminant is a *Mycoplasma* species selected from the group consisting of *M. hyorhinis, M. arginini, M. pneumoniae, M. fermentans, M. orale*, and *M. pirium*, or the bacterial contaminant is *Acholeplasma laidlawii*, or the bacterial contaminant is *Spiroplasma mirium*.

According to another embodiment of the instant disclosure, a composition comprising amniotic fluid from embryonated eggs and DNA from CHO cells is provided. In some embodiments, a lysis reagent selected from a chaotropic agent and a protease is also provided.

Other embodiments of the instant disclosure provide a composition comprising (i) purified nucleic acids from a sample selected from the group consisting of amniotic fluid, a suspension of eukaryotic cells, and a supernatant from a suspension of eukaryotic cells, and (ii) DNA from CHO cells which is free of prokaryotic DNA. In some such embodiments, the composition further comprises a first primer according to SEQ ID NO:1, a second primer according to SEQ ID NO:2, nucleotide triphosphates, and a thermostable DNA polymerase. The composition may also comprise an intercalating dye in some embodiments. Some embodiments of the instant disclosure include a use of the disclosed composition according for amplifying DNA of a prokaryotic contaminant from DNA isolated from a sample selected from the group consisting of amniotic fluid, a suspension of eukaryotic cells, and a supernatant from a suspension of eukaryotic cell.

Yet still other embodiments of the instant disclosure include a kit comprising in separate containers (i) a lysis reagent, (ii) purified DNA from CHO cells at a predefined concentration, said DNA being free of prokaryotic DNA, and (iii) a first primer according to SEQ ID NO:1 and a second primer according to SEQ ID NO:2.

Still other embodiments of the instant disclosure comprise an improved method for performing an improved polymerase chain reaction (PCR), wherein a specific amplification product with a size in the range of about 100 bp to about 1500 bp is formed by DNA polymerase-catalyzed extension of a pair of oligonucleotide primers. The primers each hybridize to a target sequence comprised in the genomic complement of the 16S-rRNA of one or more prokaryotic organism(s) and are capable of forming in PCR a specific amplification product from a first template. The PCR is conducted under predetermined conditions in a reaction mixture with a predetermined composition, and the first template comprises genomic DNA of a first eukaryotic organism and genomic DNA of the one or more prokaryotic organism(s). Also, during PCR the pair of oligonucleotide primers does not form an amplification product from a second template under the same conditions in the reaction mixture. The genomic DNA of the one or more prokaryotic organism(s) is in the second template, but genomic DNA of the first eukaryotic organism is. The improved method comprises the steps of:
  (a) providing said pair of oligonucleotide primers and genomic DNA of said first eukaryotic organism;
  (b) providing a third template comprising genomic DNA of a second eukaryotic organism which is suspected to contain genomic DNA of said one or more prokaryotic organism(s);
  (c) mixing said primer pair of (a), said third template of (b), and a measured amount of said genomic DNA of said first eukaryotic organism in the reaction mixture (Q) and performing PCR under the conditions (R); wherein the formation of a non-specific PCR amplification product is suppressed.

The following examples, set forth below, are provided for the purpose of demonstrating various embodiments of the instant disclosure and aiding in an understanding of the present disclosure. These examples are not intended to, and should not be understood as, limiting the scope or spirit of the instant disclosure in any way.

Examples

Example 1

The MYCOTOOL Kit and Assay.

The MYCOTOOL PCR *Mycoplasma* Detection Kit is an in vitro nucleic acid amplification test optimized for the detection of bacteria belonging to the Mollicutes. These include *Mycoplasma hyorhinis, M. arginini, M. pneumoniae, M. fermentans, M. orale, M. pirium, M. salivarum, M. hominis, M. synoviae, Spiroplasma mirium, S. citri*, and *Acholeplasma laidlawii*.

The MycoTool Kit comprises two subkits: Subkit 1 ("Detection Prep Kit"; Roche Applied Science Catalog No. 05184592001) and Subkit 2 ("Detection Amplification Kit"; Roche Applied Science Catalog No. 05184240001).

The kit was used exactly according to the instructions of the manufacturer.

If not stated otherwise, a liquid sample selected from (i) cell culture supernatant, (ii) a suspension of cultured cells and (iii) amniotic fluid was lysed by adding an aqueous buffer containing a guanidinium salt and proteinase K, mixing the buffer with the sample, and incubating the mixture to effect lysis.

After lysis, typically 10-250 µg per 1 ml sample CHO cell DNA was added to the lysate and mixed. The CHO cell DNA was free of any contaminating prokaryotic DNA as tested separately. Subsequently the nucleic acids were precipitated from the mixture by adding alcohol. The precipitate was recovered by centrifugation, washed with 70% ethanol and dried. The dried pellet was dissolved in the prescribed buffer and subjected to PCR analysis.

As an internal control the MYCOTOOL kit also includes a primer pair for the GAPDH housekeeping gene.

Prior to PCR amplification, the risk of amplicon contamination was reduced by applying uracil-N-glycosylase enzyme (component of the kit).

In each Example below PCR was performed exactly according to the instructions by the manufacturer. PCR products were electrophoresed on polyacrylamide gels under standard conditions. Bands were visualized with the RESOLIGHT compound and UV illumination, band detection was at 520 nm.

The primers of the MYCOTOOL kit used for detection of Mollicutes are those of SEQ ID NO:1 and SEQ ID NO:2. Control primers specific for GAPDH are also provided (SEQ ID NO:3 and SEQ ID NO:4).

Each MYCOTOOL kit further comprises a control plasmid containing *Mycoplasma* DNA, however producing a PCR fragment with a discernably different size compared to the PCR fragments amplified from isolated bacterial DNA (positive control). To this end, reference is made to Eldering, J. A., et al., Biologicals 32 (2004) 183-193, who disclose the plasmid.

Example 2

DNA from Mollicutes Species for Spiking of Samples.

All samples used in the present Examples were from cultures free of prokaryotic contaminants.

Instead of sample material infected with a Mollicutes species, DNA prepared from *Acholeplasma laidlawii* or *Mycoplasma orale* was spiked to either sample material prior to lysis, or to isolated DNA prepared from sample material (if not indicated otherwise). For the purpose of spiking DNA was prepared from reference cultures (standard conditions) of *Acholeplasma laidlawii* (ATCC 27556) and *Mycoplasma orale* (ATCC 23714). For each culture the cell titer expressed as colony forming units (cfu) was determined. Quantities of spiked DNA which were applied reflected the number of cfu determined for the respective culture from which the DNA was prepared.

Mollicutes DNA as indicated above was used in the spiking experiments described below. The size of a typical specific PCR fragment amplified from Mollicutes DNA (specific amplification product) was in the range of about 430-470 bp.

Example 3

Detection of GAPDH Genomic Target Sequences in Samples from MDCK Cell Culture (Suspended Cells).

A culture of MDCK cells free of any prokaryotic organisms and having a cell titer of $0.79 \times 10^6$ cells/ml was used. *Acholeplasma laidlawii* DNA was added to the sample at a concentration of 3 colony forming units (cfu) per 1 ml sample. Nucleic acids were isolated from the spiked sample material as specified in the instruction manual of the MYCOTOOL kit (see also Example 1). Two different nucleic acid preparations were made, the first without addition of CHO cell DNA, the second with the addition of CHO cell DNA (50 mg per 1 ml sample) to the sample material.

The preparation was repeated, however without spiking *Acholeplasma laidlawii* DNA to the sample. Again, nucleic acids were prepared with or without CHO cell DNA.

Several dilutions of the DNA preparations were made in TE buffer. An aliquot of each dilution was subjected to GAPDH-specific PCR according to the MYCOTOOL instruction manual.

Figure 2:
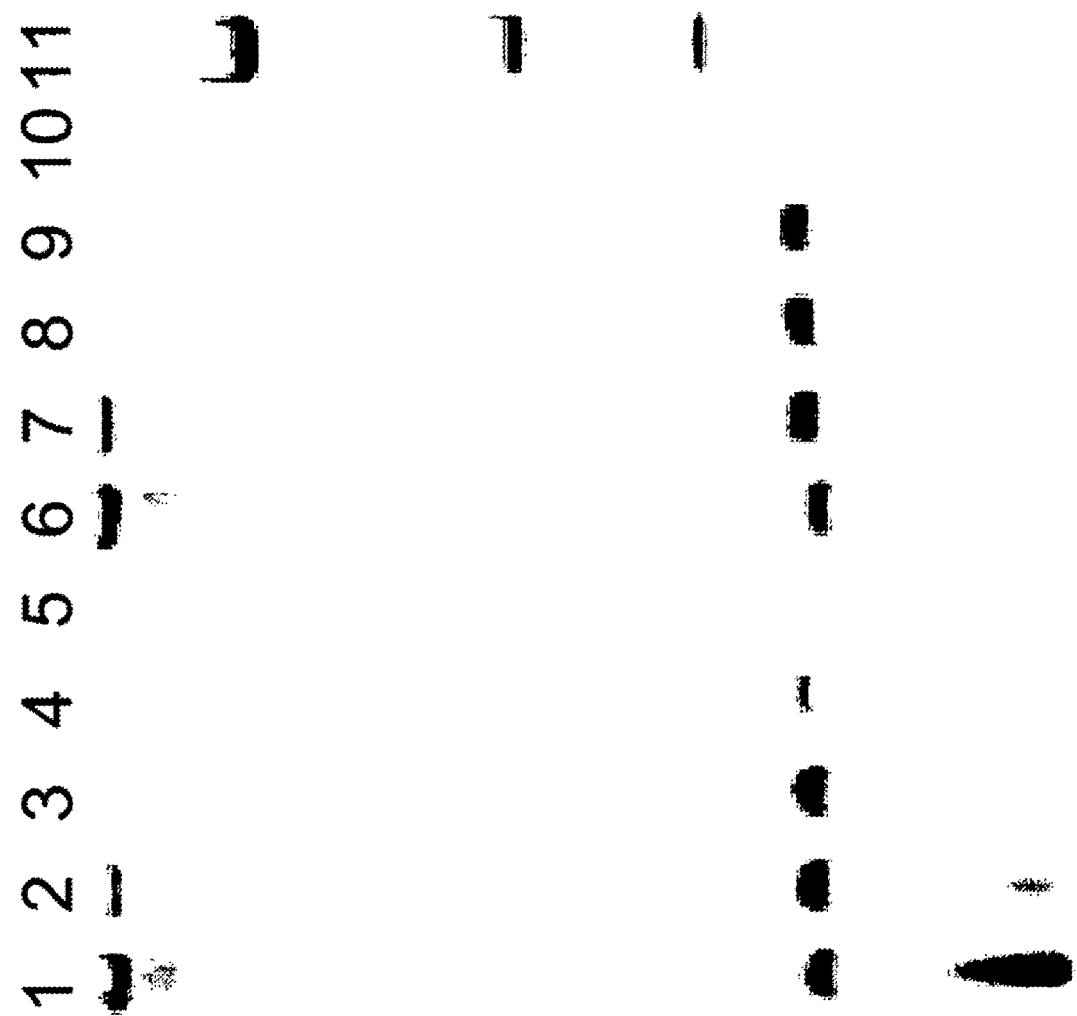
FIG. 2 is a gel showing PCR amplification products (of GAPDH-specific primers) obtained from a MDCK cell culture with the addition of CHO DNA.

FIGS. 1 and 2 show the gels with the bands indicating the PCR products which were obtained. FIG. 1 depicts the results obtained without CHO cell DNA added, FIG. 2 sows the PCR products obtained with CHO cell DNA added.

FIG. 1:

| Lane | Comment/Dilution |
|---|---|
| 1-5 | GAPDH control PCR; DNA isolated from MDCK cells; no CHO cell DNA; spiked with *A. laidlawii* DNA |
| 1 | undiluted |
| 2 | $10^{-1}$ |
| 3 | $10^{-2}$ |
| 4 | $10^{-3}$ |
| 5 | $10^{-4}$ |
| 6 | Size marker (50 bp steps) |
| 7-11 | GAPDH control PCR; DNA isolated from MDCK cells, no CHO cell DNA, not spiked |
| 7 | $10^{-1}$ |
| 8 | $10^{-2}$ |
| 9 | $10^{-3}$ |
| 10 | $10^{-4}$ |
| 11 | Size marker (50 bp steps) |

FIG. 2:

| Lane | Comment/Dilution |
|---|---|
| 1-5 | GAPDH control PCR; DNA isolated from MDCK cells, CHO cell DNA added, spiked with *A. laidlawii* DNA |
| 1 | undiluted |
| 2 | $10^{-1}$ |
| 3 | $10^{-2}$ |
| 4 | $10^{-3}$ |
| 5 | $10^{-4}$ |
| 6 | Size marker (50 bp steps) |
| 7-11 | GAPDH control PCR; DNA isolated from MDCK cells, CHO cell DNA added, not spiked |
| 7 | $10^{-1}$ |
| 8 | $10^{-2}$ |
| 9 | $10^{-3}$ |
| 10 | $10^{-4}$ |
| 11 | Size marker (50 bp steps) |

As observed, with CHO DNA added the GAPDH control bands were detectable even when PCR was performed with $10^{-4}$ dilutions.

Example 4

Detection of Target Sequences in the 16S-rRNA Complement of Prokaryotic DNA in Spiked Samples from Culture Supernatant of Adipose Stem Cells (ASC).

Figure 3:
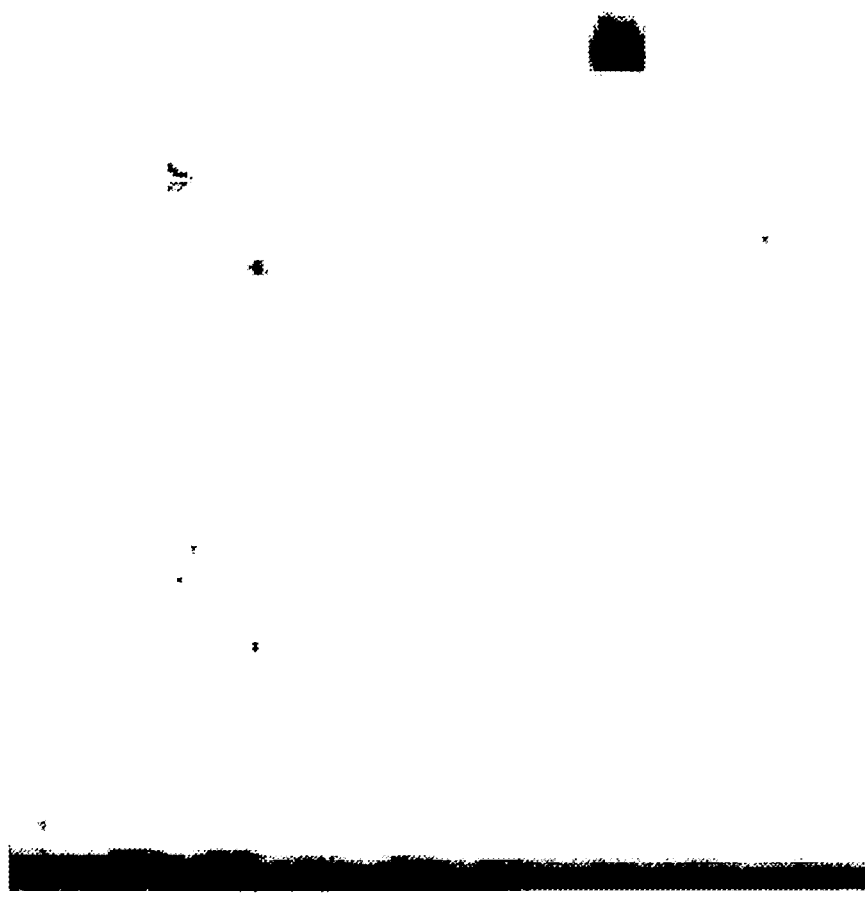
FIG. 3 is a gel showing PCR amplification products (of primers according to SEQ ID NOs: 1 and 2) obtained from Adipose Stem Cells spiked with various combinations of *Mycoplasma orale* and CHO DNA.
Figure 4:
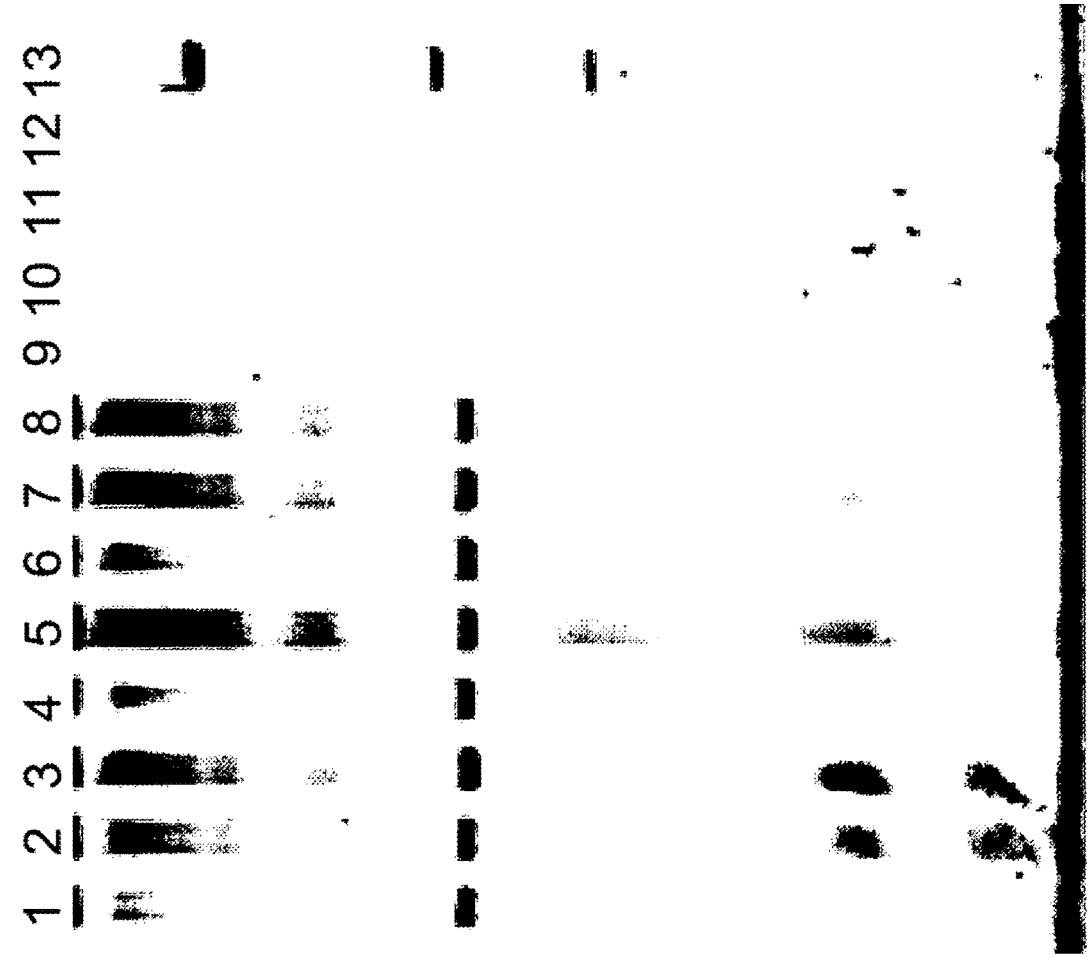
FIG. 4 is another gel showing PCR amplification products (of primers according to SEQ ID NOs: 1 and 2) obtained from Adipose Stem Cells spiked with various combinations of *Mycoplasma orale* and CHO DNA.

ASC free of any prokaryotic organisms were sedimented by centrifugation. The cleared supernatant (cell culture medium) was used for DNA isolation as specified in the instruction manual of the MYCOTOOL kit (see also Example 1). Prior to the lysis step, *Mycoplasma orale* DNA was added to the sample at a concentration of 3 colony forming units (cfu) per 1 ml sample. The sample was then divided into two equal volumes. To one aliquot CHO cell DNA was added at a concentration of 100 mg per 1 ml of supernatant. Total DNA was isolated from both aliquots separately. Several PCR reactions were performed with aliquots of each DNA preparation. FIGS. 3 and 4 show the gels with the amplification products obtained by PCR and after electrophoresing the DNA fragments.

As observed, the addition of CHO cell DNA made the MYCOTOOL test more robust in that *Mycoplasma* DNA was detected in all spiked samples tested. On the other hand, without CHO cell DNA only 1 of 8 PCR reactions successfully amplified a fragment specific for the *Mycoplasma* target DNA.

FIG. 3:

| Lane | Comment/Dilution |
|---|---|
| 1-8 | Primers as in SEQ ID NO: 1 and SEQ ID NO: 2; DNA isolated from ASC, spiked with *M. orale* DNA, no CHO cell DNA |
| 1-8 | Primers as in SEQ ID NO: 1 and SEQ ID NO: 2; PCR with 8 independently drawn aliquots |
| 6 | The size of the band is in line with the size range observed for a specific target DNA amplification product |

FIG. 4:

| Lane | Comment/Dilution |
|---|---|
| 1-8 | Primers as in SEQ ID NO: 1 and SEQ ID NO: 2; DNA isolated from ASC, spiked with *M. orale* DNA, with CHO cell DNA added |
| 1-8 | Primers as in SEQ ID NO: 1 and SEQ ID NO: 2; PCR with 8 independently drawn aliquots |
| 9-12 | Primers as in SEQ ID NO: 1 and SEQ ID NO: 2; PCR with buffer ("no template" control) |
| 13 | Size marker (50 bp steps) |

As expected, in the case where CHO cell DNA is absent it can be seen (FIG. 3) that non-specific PCR fragments are substantially absent (lane 1 in FIG. 3 being a possible exception), demonstrating that PCR artifacts are not commonly produced by the MYCOTOOL assay. However, these results demonstrate that addition of CHO cell DNA as described herein does not lead to unspecific amplification products as can be seen in FIG. 4.

Example 5

Detection of Target Sequences in the 16S-rRNA Complement of Prokaryotic DNA in Spiked Aqueous Buffer.

Figure 5:
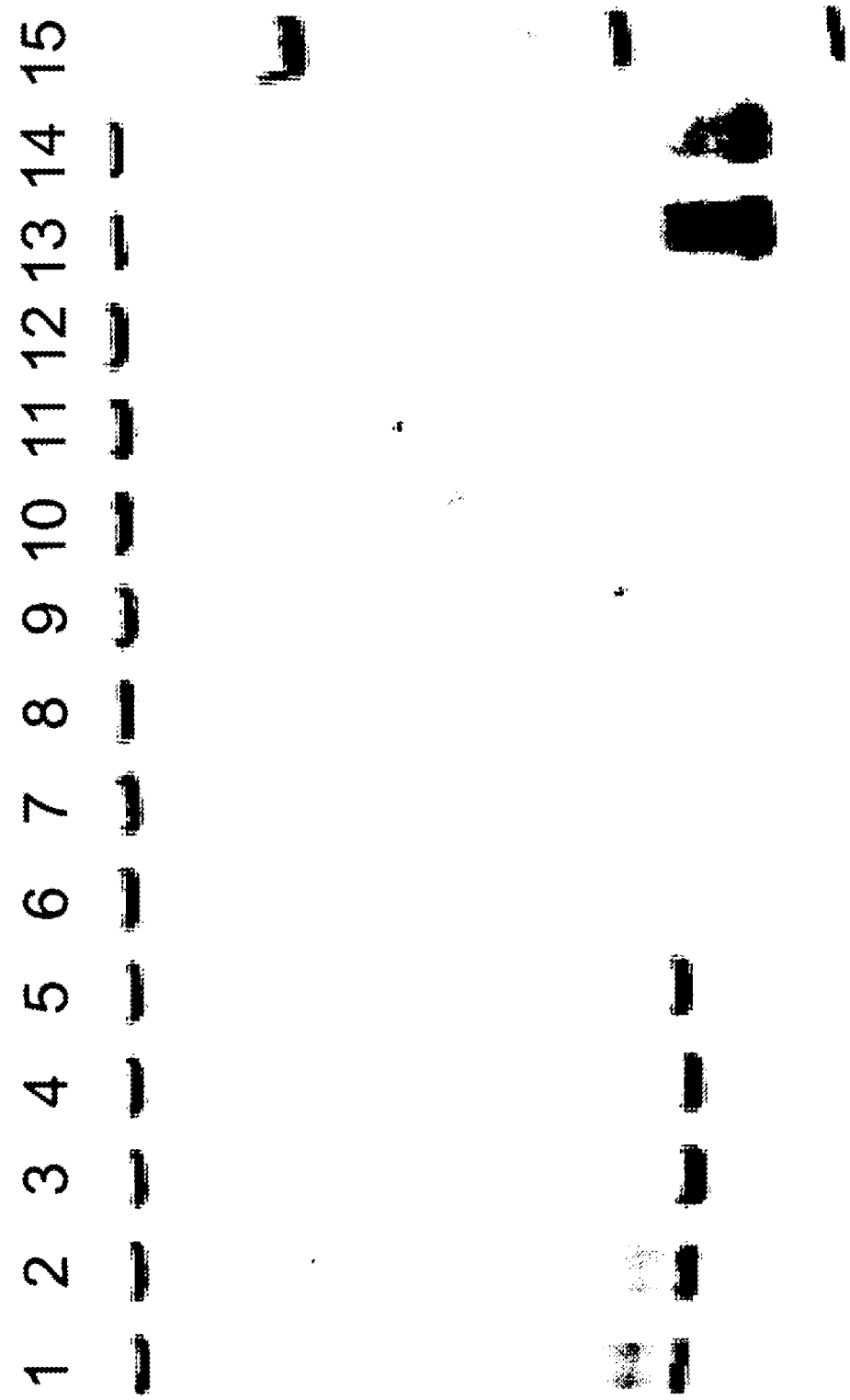
FIG. 5 is a gel showing PCR amplification products (of primers according to SEQ ID NOs: 1 and 2) obtained from buffer spiked with various combinations of *Acholeplasma laidlawii* DNA and CHO DNA.
Figure 6:
FIG. 6 is another gel showing PCR amplification products (of primers according to SEQ ID NOs: 1 and 2) obtained from buffer spiked with various combinations of *Acholeplasma laidlawii* DNA and CHO DNA.

10 mM TrisHCl buffer pH 7.5 free of any contaminants was spiked with *A. laidlawii* DNA at a concentration of 1 or 10 cfu per 1 ml of buffer. Spiked and unspiked buffer was mixed with CHO cell DNA to yield a concentration of 80 μg per 1 ml of buffer. In addition spiked and unspiked buffer without CHO cell DNA was prepared. From each spiked and unspiked preparation DNA was prepared according to the MYCOTOOL protocol. Several PCR reactions were performed with aliquots of each DNA preparation. In addition, PCR was performed with an aliquot of Tris buffer containing about 10 copies of the control plasmid which is part of the MYCOTOOL kit (positive control). FIGS. 5 and 6 show the gels with the amplification products obtained by PCR and after electrophoresing the DNA fragments.

FIG. 5:

| Lane | Comment/Dilution |
|---|---|
| 1-8 | Primers as in SEQ ID NO: 1 and SEQ ID NO: 2; Tris buffer spiked with *A. laidlawii* DNA, no CHO cell DNA |
| 1-4 | 10 cfu *A. laidlawii* DNA |
| 5-8 | 1 cfu *A. laidlawii* DNA |
| 9-12 | Primers as in SEQ ID NO: 1 and SEQ ID NO: 2; Tris buffer, not spiked, no CHO cell DNA |
| 13, 14 | Primers as in SEQ ID NO: 1 and SEQ ID NO: 2; Tris buffer, about 10 copies of positive control plasmid (part of MYCOTOOL kit) per PCR reaction mixture, no CHO cell DNA |
| 15 | Size marker (50 bp steps) |

FIG. 6:

| Lane | Comment/Dilution |
|---|---|
| 1-8 | Primers as in SEQ ID NO: 1 and SEQ ID NO: 2; Tris buffer spiked with *A. laidlawii* DNA, with CHO cell DNA added |
| 1-4 | 10 cfu *A. laidlawii* DNA |
| 5-8 | 1 cfu *A. laidlawii* DNA |
| 9-12 | Primers as in SEQ ID NO: 1 and SEQ ID NO: 2; Tris buffer, not spiked, with CHO cell DNA added |
| 13, 14 | Primers as in SEQ ID NO: 1 and SEQ ID NO: 2; Tris buffer, about 10 copies of positive control plasmid (part of MYCOTOOL kit) per PCR reaction mixture, with CHO cell DNA added |
| 15 | Size marker (50 bp steps) |

While the PCR had no problems detecting the *A. laidlawii* DNA corresponding to 10 cfu, detection of 1 cfu was markedly improved in the presence of CHO cell DNA.

The lanes with the positive control plasmid illustrate the discernible size difference compared with the specific amplification products of *A. laidlawii* target sequence.

Example 6

Detection of Target Sequences in the 16S-rRNA Complement of Prokaryotic DNA in Spiked Samples from Culture Vero Cell Culture (Suspended Cells).

Suspensions of Vero cells with a cell titer in the range of $10^5$ to $10^6$ cells per ml from a culture which was free of any prokaryotic organisms were spiked with *A. laidlawii* or *M. orale* DNA at a concentration of 3 or 10 cfu per 1 ml of cell suspension. To the culture spiked with 3 cfu/ml CHO cell DNA was added at a concentration of 10, 30, 50, 70, 85, 100, and 150 µg per 1 ml of cell suspension.

Figure 7:
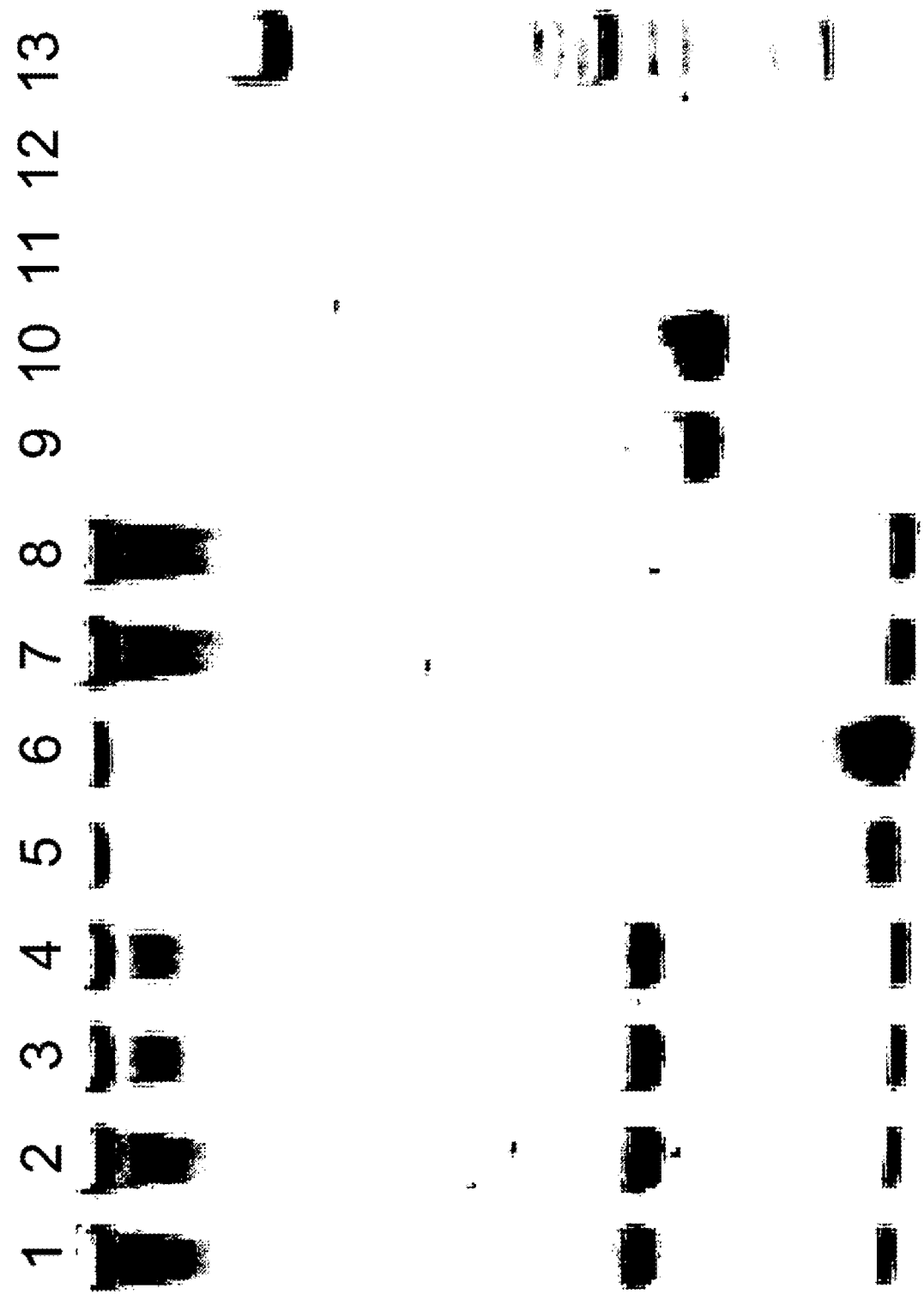
FIG. 7 is a gel showing PCR amplification products (of primers according to SEQ ID NOs: 1 and 2) obtained from samples from Vero cells spiked with various combinations of *Acholeplasma laidlawii* DNA, *Mycoplasma orale* DNA, and CHO DNA.
Figure 8:
FIG. 8 is another gel showing PCR amplification products (of primers according to SEQ ID NOs: 1 and 2) obtained from samples from Vero cells spiked with various combinations of *Acholeplasma laidlawii* DNA, *Mycoplasma orale* DNA, and CHO DNA.
Figure 9:
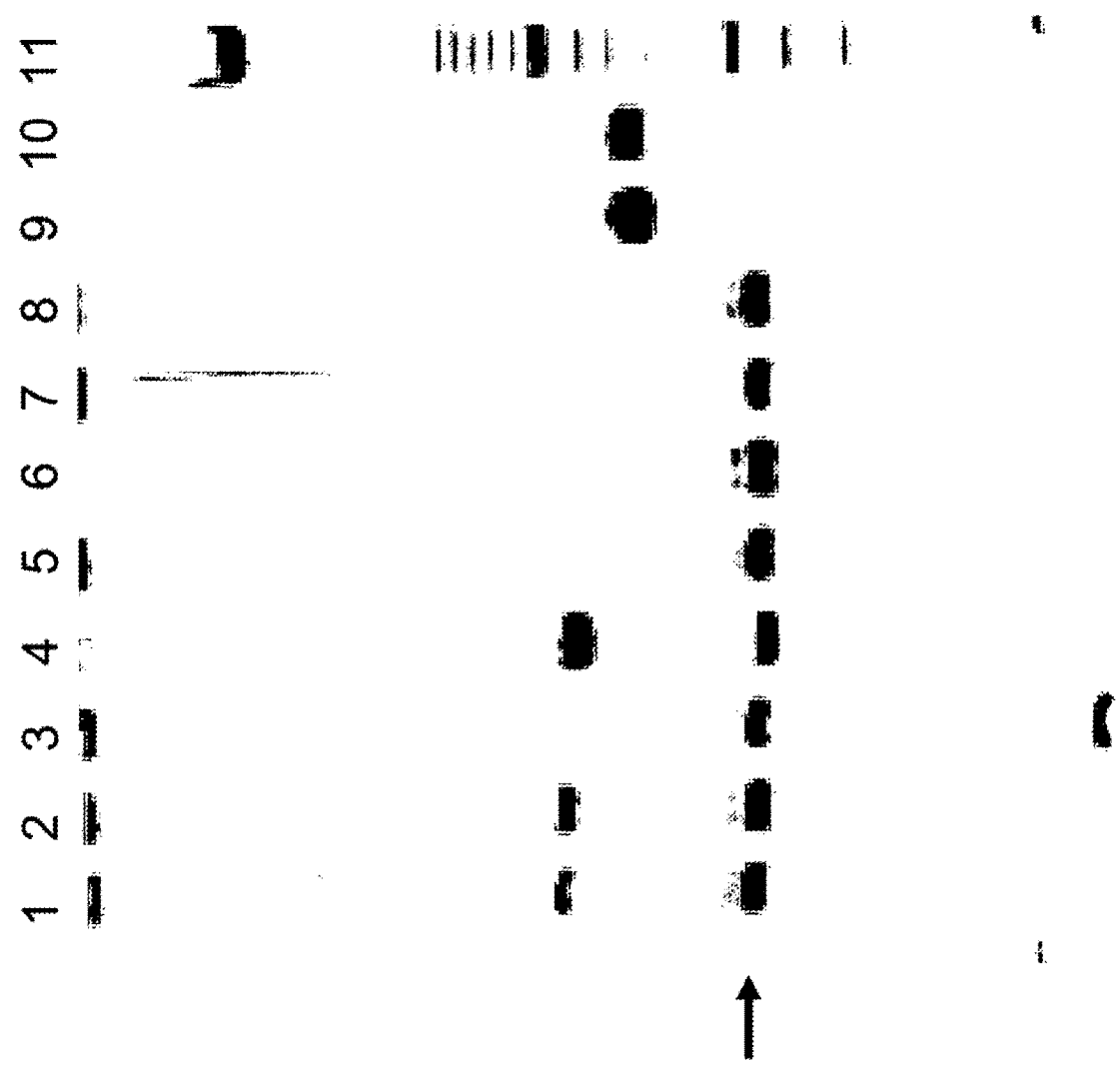
FIG. 9 is a gel showing PCR amplification products (of primers according to SEQ ID NOs: 1 and 2) obtained from samples from embryonated chicken eggs inoculated with various combinations of *Acholeplasma laidlawii* and CHO DNA.
Figure 10:
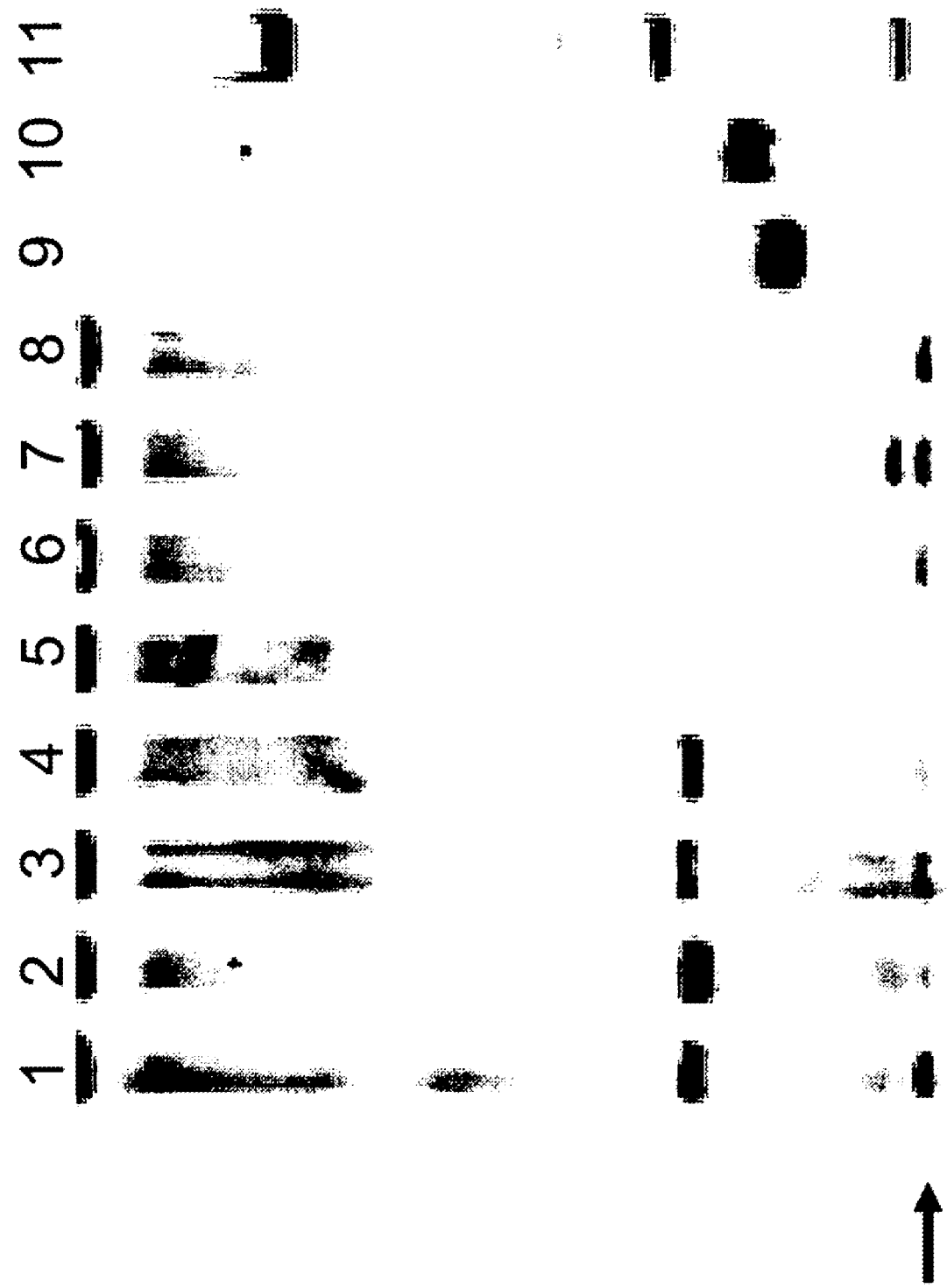
FIG. 10 is another gel showing PCR amplification products (of primers according to SEQ ID NOs: 1 and 2) obtained from samples from embryonated chicken eggs inoculated with various combinations of *Acholeplasma laidlawii* and CHO DNA.
Figure 11:
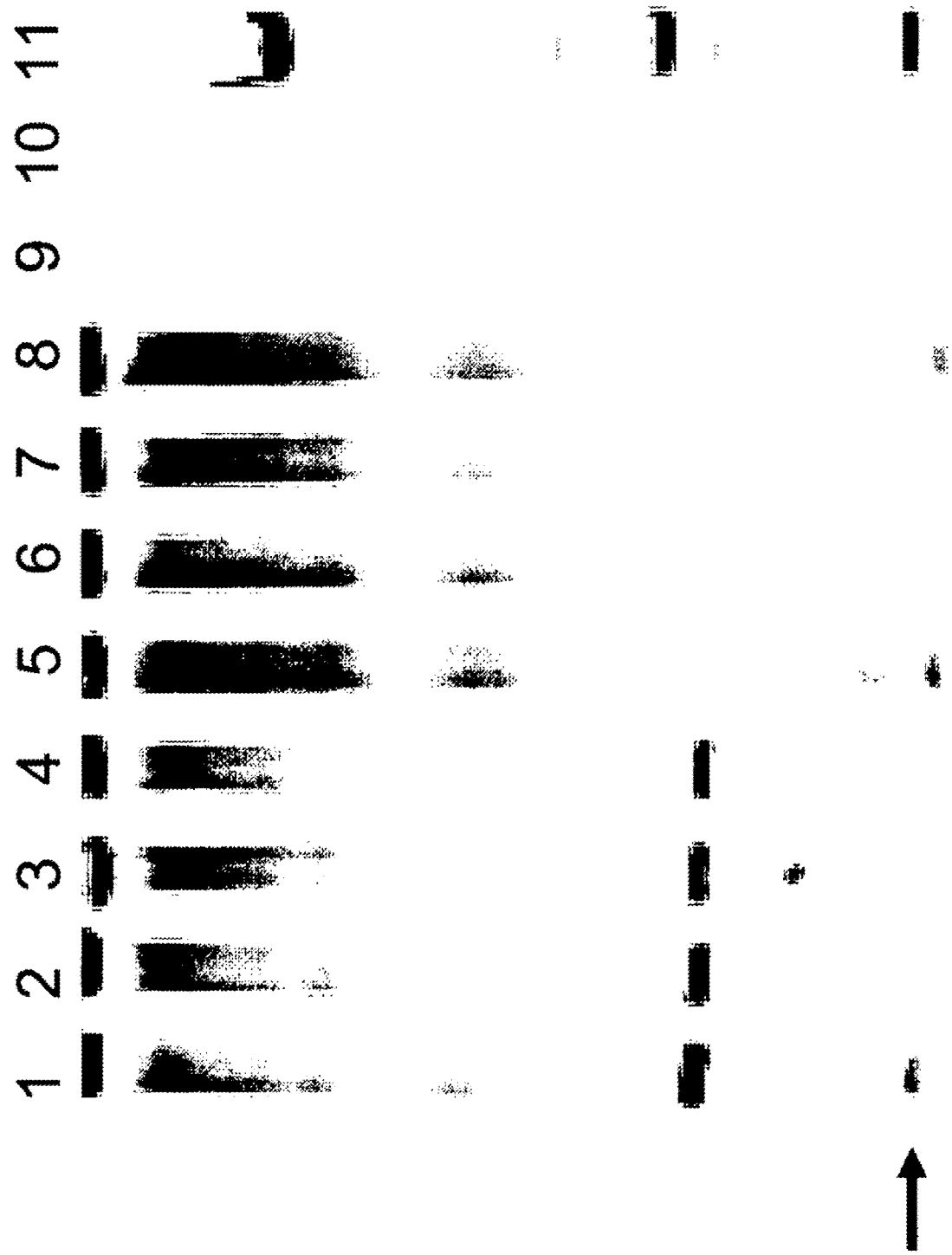
FIG. 11 is yet another gel showing PCR amplification products (of primers according to SEQ ID NOs: 1 and 2) obtained from samples from embryonated chicken eggs inoculated with various combinations of *Acholeplasma laidlawii* and CHO DNA.
Figure 12:
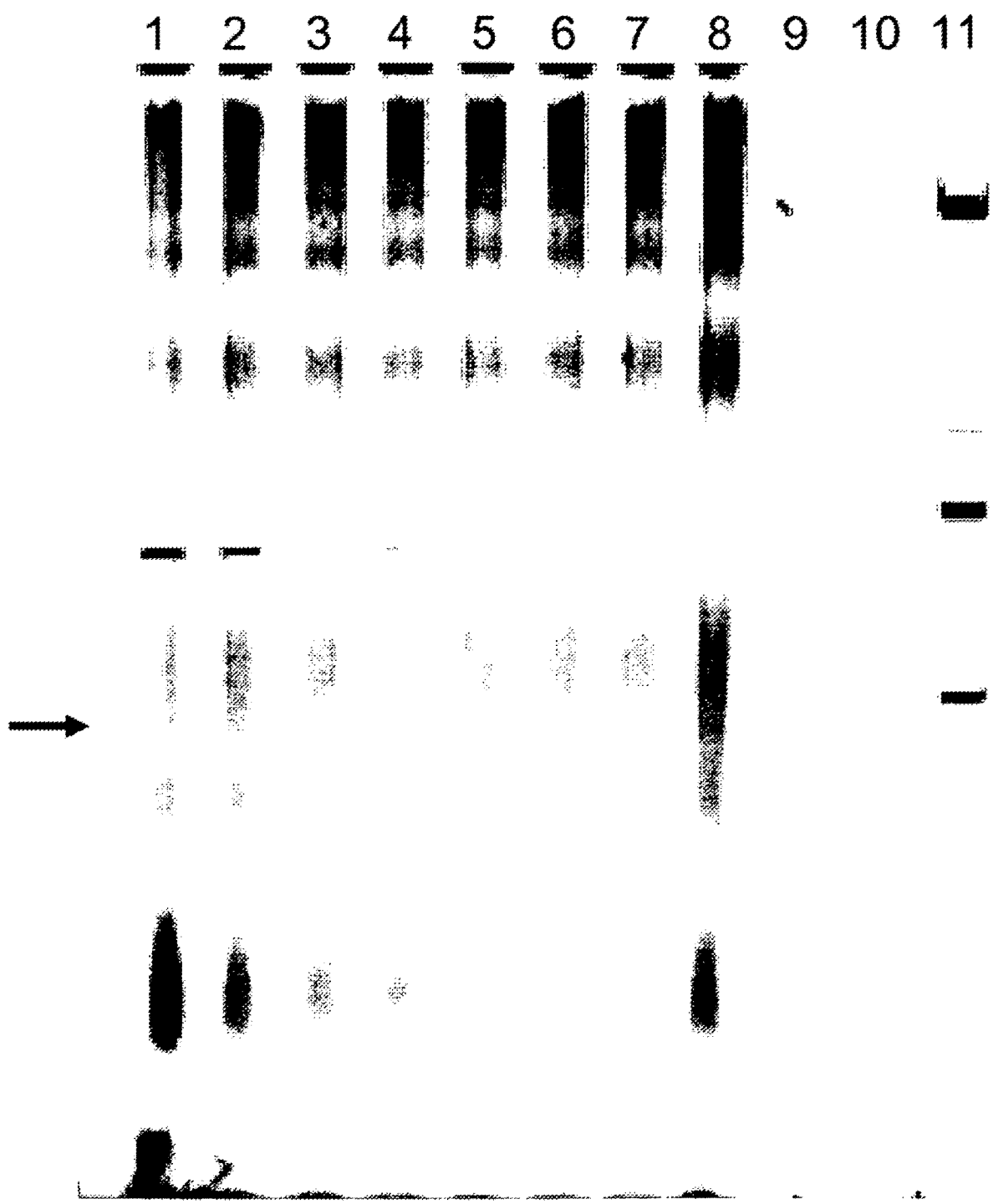
FIG. 12 is another gel showing PCR amplification products (of primers according to SEQ ID NOs: 1 and 2) obtained from samples from embryonated chicken eggs inoculated with various combinations of *Acholeplasma laidlawii* and CHO DNA.

From each spiked suspension as well as from unspiked suspensions of Vero cells alone DNA was prepared according to the MYCOTOOL protocol. Several PCR reactions were performed with aliquots of each DNA preparation. In addition, PCR was performed with an aliquot of Tris buffer (10 mM TrisHCl buffer pH 7.5) containing about 10 copies of the control plasmid which is part of the MYCOTOOL kit (positive control). FIGS. 7 and 8 show the gels with the amplification products obtained by PCR and after electrophoresing the DNA fragments. The samples shown in FIG. 8 contained CHO cell DNA at a concentration of 150 µg per 1 ml of cell suspension. Comparable results were obtained when using the concentrations of 10, 30, 50, 70, 85, and 100 µg CHO cell DNA per 1 ml of cell suspension.

FIG. 7:

| Lane | Comment/Dilution |
|---|---|
| 1-4 | Primers as in SEQ ID NO: 1 and SEQ ID NO: 2; Vero cell suspension spiked with *A. laidlawii* DNA, no CHO cell DNA |
| 1-4 | 10 cfu *A. laidlawii* DNA |
| 5-8 | Primers as in SEQ ID NO: 1 and SEQ ID NO: 2; Vero cell suspension, not spiked, no CHO cell DNA |
| 9, 10 | Primers as in SEQ ID NO: 1 and SEQ ID NO: 2; Tris buffer, about 10 copies of positive control plasmid (part of MYCOTOOL kit) per PCR reaction mixture, no CHO cell DNA |
| 11, 12 | Primers as in SEQ ID NO: 1 and SEQ ID NO: 2; PCR with buffer ("no template" control) |
| 13 | Size marker (50 bp steps) |

FIG. 8:

| Lane | Comment/Dilution |
|---|---|
| 1-4 | Primers as in SEQ ID NO: 1 and SEQ ID NO: 2; Vero cell suspension spiked with *A. laidlawii* DNA, with CHO cell DNA added |
| 1-4 | 3 cfu *A. laidlawii* DNA |
| 5-8 | Primers as in SEQ ID NO: 1 and SEQ ID NO: 2; Vero cell suspension, not spiked, with CHO cell DNA added |
| 9, 10 | Primers as in SEQ ID NO: 1 and SEQ ID NO: 2; Tris buffer, about 10 copies of positive control plasmid (part of MYCOTOOL kit) per PCR reaction mixture, with CHO cell DNA added |
| 11, 12 | Primers as in SEQ ID NO: 1 and SEQ ID NO: 2; PCR with buffer ("no template" control) |
| 13 | Size marker (50 bp steps) |

Notably, some non-specific (artifact) PCR products were obtained in the absence of CHO cell DNA (see FIG. 7). The similarity in some cases of the size of these artifact bands to the size of the specific amplification products (lanes 1-4 in FIG. 7) was noted. Surprisingly, no unspecific PCR amplification products were produced in in the presence of CHO cell DNA (FIG. 8, lanes 1-4).

Example 7

Detection of Target Sequences in the 16S-rRNA Complement of Prokaryotic DNA in "Inoculated" Samples of Allantois Fluid from Embryonated Chicken Eggs.

Allantois fluid free of *mycoplasma* contamination was harvested from embryonated chicken eggs (9 to 11 days) which were inoculated with a viral vaccine strain.

A liquid culture of *A. laidlawii* with a titer of $2.45 \times 10^3$ cfu was diluted with TE buffer 1:1,000. An aliquot of this dilution was diluted 1:10 with allantois fluid. A volume of 12.2 µl of this 1:10,000 inoculum was added per 1 ml of allantois fluid to result in an equivalent titer of 3 cfu per 1 ml of inoculated allantois fluid. The inoculated allantois fluid was subjected to DNA isolation without further incubation, i.e. the bacteria were not allowed to grow in the allantois fluid.

Four different samples were provided: (i) inoculated allantois fluid without CHO cell DNA, (ii) non inoculated allantois fluid without CHO cell DNA, (iii) inoculated allantois fluid with CHO cell DNA added, and (iv) non inoculated allantois fluid with CHO cell DNA added. In the samples of (iii) and (iv) the concentration of the CHO cell DNA was 208 mg per 1 ml of allantois fluid.

From each inoculated and non-inoculated sample (i-iv) DNA was prepared according to the MYCOTOOL protocol. Several PCR reactions were performed with aliquots of each DNA preparation. In addition, PCR was performed with an aliquot of Tris buffer (10 mM TrisHCl buffer pH 7.5) containing about 10 copies of the control plasmid which is part of the MYCOTOOL kit (positive control).

Again, the effect that the presence of CHO cell DNA (a) suppresses non-specific PCR amplification products and (b) increases sensitivity of PCR detection could be verified.

Example 8

Detection of Target Sequences in the 16S-rRNA Complement of Prokaryotic DNA in "Inoculated" Samples of Allantois Fluid from Embryonated Chicken Eggs, Addition of Different Concentrations of CHO Cell DNA to the PC Reaction Mixture.

The experiment was conducted as described in Example 7 with the exception that no CHO cell DNA was added prior to DNA purification. Instead, CHO cell DNA was added to the reaction mixture prior to starting PCR. The concentration of CHO cell DNA in the reaction mixture was 0, 2.5, 5, and 10 µg per 50 µl (volume of the PCR reaction mixture). This corresponds to 0 µg/µl, 0.05 µg/µl, 0.1 µg/µl, and 0.2 µg/µl in the final reaction mixture, i.e. the reaction mixture just prior to starting the PCR reaction. FIGS. 9-12 show the results (the arrow indicates the region of the get in which non-specifically amplified PCR products migrate).

FIG. 9:

| Lane | Comment/Dilution |
|---|---|
| 1-4 | Primers as in SEQ ID NO: 1 and SEQ ID NO: 2; allantois fluid "inoculated" with *A. laidlawii*, no CHO cell DNA |
| 1-4 | 3 cfu *A. laidlawii* DNA |
| 5-8 | Primers as in SEQ ID NO: 1 and SEQ ID NO: 2; allantois fluid, not inoculated, no CHO cell DNA |

| Lane | Comment/Dilution |
|---|---|
| 9, 10 | Primers as in SEQ ID NO: 1 and SEQ ID NO: 2; Tris buffer, about 10 copies of positive control plasmid (part of MYCOTOOL kit) per PCR reaction mixture, no CHO cell DNA |
| 11 | Size marker (50 bp steps) |

FIG. 10:

| Lane | Comment/Dilution |
|---|---|
| 1-4 | Primers as in SEQ ID NO: 1 and SEQ ID NO: 2; allantois fluid "inoculated" with *A. laidlawii*, 2.5 μg/50 μl CHO cell DNA |
| 1-4 | 3 cfu *A. laidlawii* DNA |
| 5-8 | Primers as in SEQ ID NO: 1 and SEQ ID NO: 2; allantois fluid, not inoculated, 2.5 μg/50 μl CHO cell DNA |
| 9, 10 | Primers as in SEQ ID NO: 1 and SEQ ID NO: 2; Tris buffer, about 10 copies of positive control plasmid (part of MYCOTOOL kit) per PCR reaction mixture, no CHO cell DNA |
| 11 | Size marker (50 bp steps) |

FIG. 11:

| Lane | Comment/Dilution |
|---|---|
| 1-4 | Primers as in SEQ ID NO: 1 and SEQ ID NO: 2; allantois fluid "inoculated" with *A. laidlawii*, 5 μg/50 μl CHO cell DNA |
| 1-4 | 3 cfu *A. laidlawii* DNA |
| 5-8 | Primers as in SEQ ID NO: 1 and SEQ ID NO: 2; allantois fluid, not inoculated, 5 μg/50 μl CHO cell DNA |
| 9, 10 | Primers as in SEQ ID NO: 1 and SEQ ID NO: 2; PCR with buffer ("no template" control) |
| 11 | Size marker (50 bp steps) |

FIG. 12:

| Lane | Comment/Dilution |
|---|---|
| 1-4 | Primers as in SEQ ID NO: 1 and SEQ ID NO: 2; allantois fluid "inoculated" with *A. laidlawii*, 10 μg/50 μl CHO cell DNA |
| 1-4 | 3 cfu *A. laidlawii* DNA |
| 5-8 | Primers as in SEQ ID NO: 1 and SEQ ID NO: 2; allantois fluid, not inoculated, 10 μg/50 μl CHO cell DNA |
| 9, 10 | Primers as in SEQ ID NO: 1 and SEQ ID NO: 2; PCR with buffer ("no template" control) |
| 11 | Size marker (50 bp steps) |

Example 9

Detection of Target Sequences in the 16S-rRNA Complement of Prokaryotic DNA in Spiked Aqueous Buffer.

Figure 13:
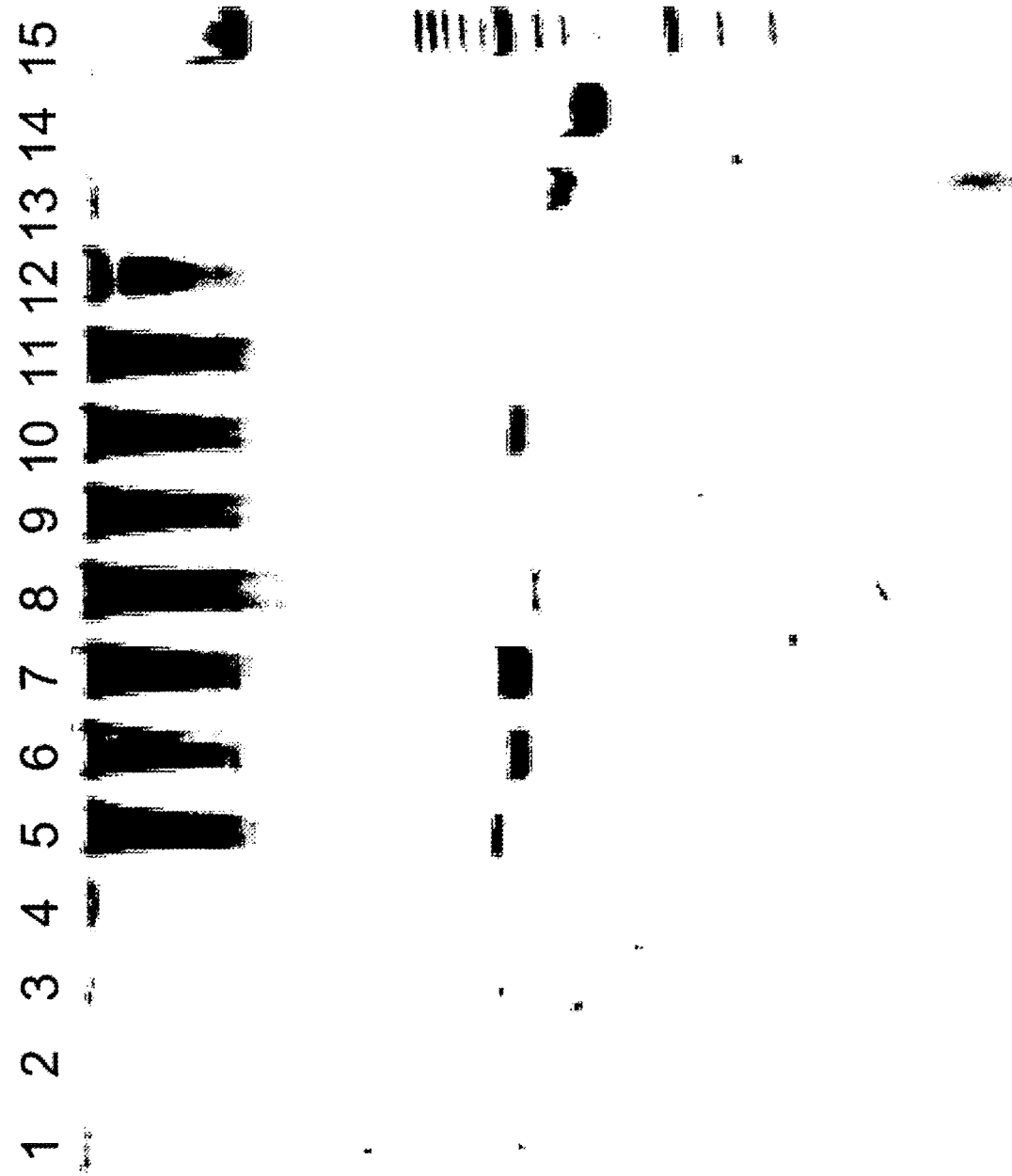
FIG. 13 is a gel showing PCR amplification products (of primers according to SEQ ID NOs: 1 and 2) obtained from buffer spiked with various combinations of *Acholeplasma laidlawii* DNA and calf thymus DNA.

The experiment was conducted as described in Example 5 with the exception that the concentration of *A. laidlawii* DNA was 3 cfu per 1 ml of buffer and instead of CHO cell DNA calf thymus was added at a concentration of 200 μg per 1 ml of buffer prior to DNA purification. FIG. 13 shows the results.

FIG. 13:

| Lane | Comment/Dilution |
|---|---|
| 1-8 | Primers as in SEQ ID NO: 1 and SEQ ID NO: 2; Tris buffer spiked with *A. laidlawii* DNA, |
| 1-4 | 3 cfu *A. laidlawii* DNA, no calf thymus DNA |
| 5-8 | 1 cfu *A. laidlawii* DNA, with calf thymus DNA added |

| Lane | Comment/Dilution |
|---|---|
| 9-12 | Primers as in SEQ ID NO: 1 and SEQ ID NO: 2; Tris buffer unspiked, with calf thymus DNA added |
| 13, 14 | Primers as in SEQ ID NO: 1 and SEQ ID NO: 2; Tris buffer, about 10 copies of positive control plasmid (part of MYCOTOOL kit) per PCR reaction mixture, no calf thymus DNA |
| 15 | Size marker (50 bp steps) |

Notably, the PCR fragments generated in the presence of calf thymus DNA show a certain variation in size, unlike the fragments produced in the presence of CHO cell DNA, e.g. those shown in FIG. 6 (in particular).

Based on these results, calf thymus DNA does not appears to be suited to suppress the formation of PCR artifacts. These results may demonstrate that CHO cell DNA's (rather than calf thymus DNA or other similarly suited eukaryotic genomic DNAs) ability to provide the desired effect is due to the fact that the MYCOTOOL PCR is based on the primers of SEQ ID NO:1 and SEQ ID NO:2 and was initially adapted to CHO cell cultures and culture supernatants. During optimization of the MYCOTOOL kit, it was not evident that the genomic DNA of the CHO cells provided a "background" which for the primers appears to beneficial in that the "background" apparently suppresses the formation of artifacts. Genomic DNA from other species is different in composition and apparently not able to suppress formation of non-specific artifacts (or less efficient in doing so).

Example 10

Detection of Target Sequences in the 16S-rRNA Complement of Prokaryotic DNA in "Inoculated" Samples of Allantois Fluid from Embryonated Chicken Eggs, Addition of Calf Thymus DNA.

The experiment was conducted as described in Example 7 with the exception that instead of CHO cell DNA, calf thymus was added prior to DNA purification.

Four different samples were provided: (i) inoculated allantois fluid without calf thymus DNA, (ii) non inoculated allantois fluid without calf thymus DNA, (iii) inoculated allantois fluid with calf thymus DNA added, and (iv) non inoculated allantois fluid with calf thymus DNA added. In the samples of (iii) and (iv) the concentration of the calf thymus DNA was 200 mg per 1 ml of allantois fluid.

Figure 14:
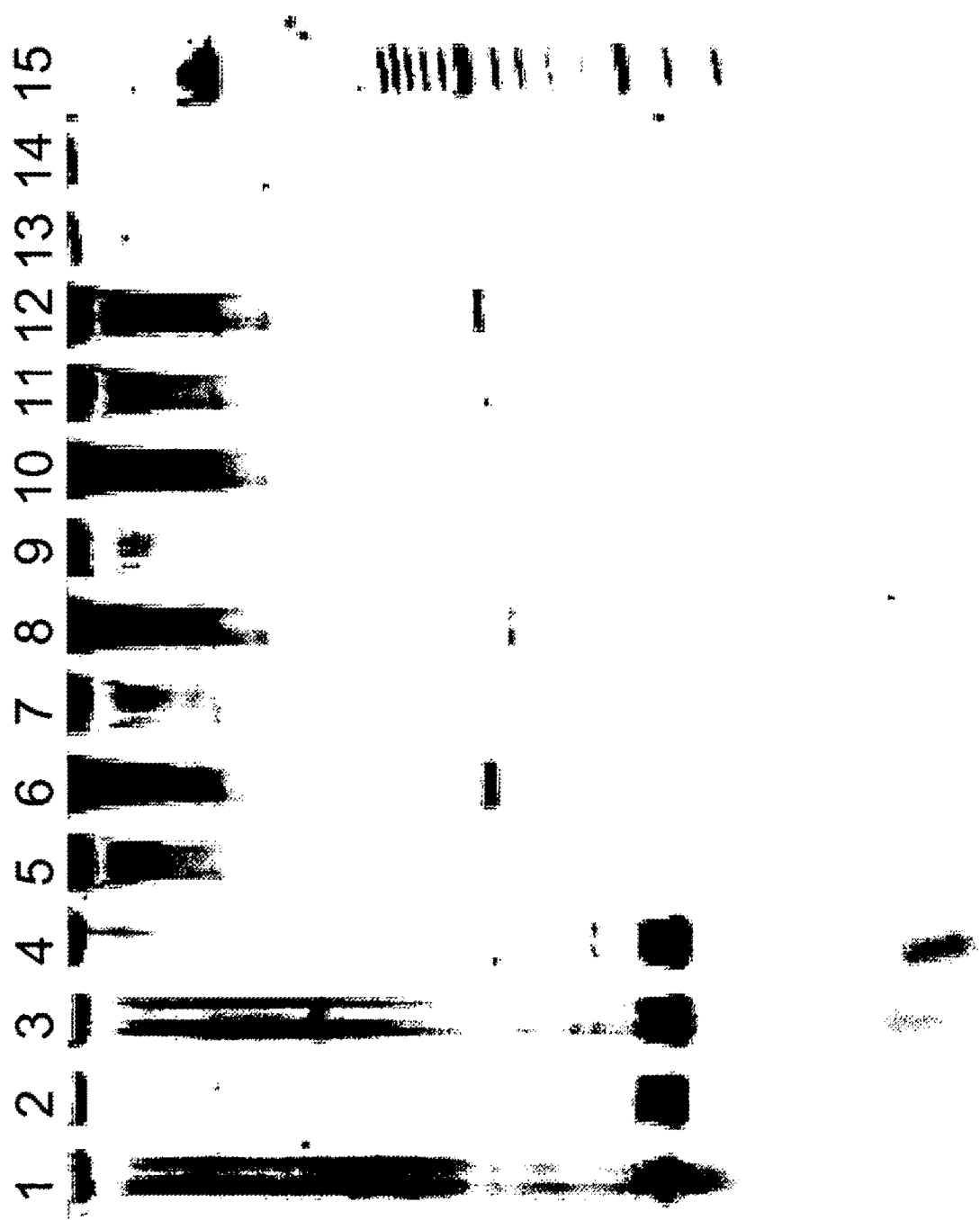
FIG. 14 is a gel showing PCR amplification products (of primers according to SEQ ID NOs: 1 and 2) obtained from samples from embryonated chicken eggs inoculated with various combinations of *Acholeplasma laidlawii* and calf thymus DNA.

FIG. 14 shows the results.

FIG. 14:

| Lane | Comment/Dilution |
|---|---|
| 1-8 | Primers as in SEQ ID NO: 1 and SEQ ID NO: 2; allantois fluid "inoculated" with *A. laidlawii*, with calf thymus DNA added |
| 1-4 | 3 cfu *A. laidlawii* DNA |
| 5-8 | Primers as in SEQ ID NO: 1 and SEQ ID NO: 2; allantois fluid, not inoculated, with calf thymus DNA added |
| 9-12 | Primers as in SEQ ID NO: 1 and SEQ ID NO: 2; Tris buffer, no inoculum, with calf thymus DNA added |
| 13, 14 | Primers as in SEQ ID NO: 1 and SEQ ID NO: 2; PCR with buffer ("no template" control) |
| 15 | Size marker (50 bp steps) |

Basically, the conclusion is similar as in Example 9. Again, non-specific amplification products were produced, in contrast to PCR in the presence of CHO cell DNA While the foregoing disclosure has been described in some detail for purposes of clarity and understanding, it will be appreciated by one skilled in the art, from a reading of the disclosure that various changes in form and detail can be made without departing from the true scope of the invention in the appended claims.

All publications, patents and applications are herein incorporated by reference in their entirety to the same extent as if each such reference was specifically and individually indicated to be incorporated by reference in its entirety.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method for determining the presence or absence of a bacterial contaminant in a sample with biological material, the bacterial contaminant being selected from the group consisting of *Mycoplasma hyorhinis, Mycoplasma arginini, Mycoplasma pneumonia, Mycoplasma fermentans, Mycoplasma orale, Mycoplasma pirium, Acholeplasma laidlawii* and *Spiroplasma mirium*, and said method comprising the steps of
    (a) processing the sample and purifying nucleic acids from the processed sample; followed by
    (b) forming a composition for a PCR, the composition including
        a first primer according to SEQ ID NO:1,
        a second primer according to SEQ ID NO:2, and
        the purified nucleic acids of step (a) or a measured fraction thereof as a template; followed by
    (c) performing a polymerase chain reaction (PCR) with the composition of step (b); followed by
    (d) detecting the presence or absence of an amplified target sequence, wherein the presence of said amplified target sequence indicates the presence of the bacterial contaminant in the sample, and the absence of said amplified target sequence indicates the absence of the bacterial contaminant in the sample;
    wherein relative to the sample a predetermined amount of total DNA from about $5 \times 10^6$ Chinese Hampster Ovary (CHO) cells is added per ml of the sample to (i) the sample, or (ii) the processed sample of step (a), or (iii) the purified nucleic acids obtained in step (a), or (iv) the composition of step (b), whereby the added DNA from CHO cells reduces unspecific amplification in step (c).

2. The method of claim 1, wherein the predetermined amount of total DNA from CHO cells is in the range of 10 µg/ml of sample to 250 µg/ml of sample.

3. The method of claim 1, wherein the sample is selected from the group consisting of cell culture medium with cultured cells, cell-free culture supernatant, and amniotic fluid.

4. The method of claim 3, wherein the sample is amniotic fluid.

5. The method of claim 4, wherein the amniotic fluid is from embryonated eggs.

6. The method of claim 1, wherein the added DNA from CHO cells is free of prokaryotic DNA.

\* \* \* \* \*

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Primer (forward) for the detection of
      Mycoplasma and related species

<400> SEQUENCE: 1
ggcgaatggg tgagtaacac g                                              21

<210> SEQ ID NO 2
<211> LENGTH: 22
<212> TYPE: DNA
<213> ORGANISM: Artificial Sequence
<220> FEATURE:
<223> OTHER INFORMATION: Primer (reverse) for the detection of
      Mycoplasma and related species

<400> SEQUENCE: 2
cggataacgc ttgcgaccta tg                                             22

<210> SEQ ID NO 3
<211> LENGTH: 21
<212> TYPE: DNA
<213> ORGANISM: Artificial Sequence
<220> FEATURE:
<223> OTHER INFORMATION: Primer (forward) for the detection of the
      Glyceraldehyde 3-phosphate dehydrogenase gene in Chinese hamster
      ovary cells

<400> SEQUENCE: 3
caaaggcaca gtcaaggctg a                                              21

<210> SEQ ID NO 4
<211> LENGTH: 21
<212> TYPE: DNA
<213> ORGANISM: Artifical Sequence
<220> FEATURE:
<223> OTHER INFORMATION: Primer (reverse) for the detection of the
      Glyceraldehyde 3-Phosphate dehydrogenase gene in Chinese hamster
      ovary cells

<400> SEQUENCE: 4
tggtgaagac gccagtagat t                                              21